United States Patent [19]

Jendralla

[11] Patent Number: 5,621,128
[45] Date of Patent: Apr. 15, 1997

[54] HALOGENATED BIPHENYL-2,2'-DIYLBISDIPHENYLPHOSPHINES, THEIR PREPARATION AND THEIR USE

[75] Inventor: Joachim-Heiner Jendralla, Frankfurt, Germany

[73] Assignee: Hoechst Aktiengesellschaft, Frankfurt am Main, Germany

[21] Appl. No.: 495,978

[22] Filed: Jun. 28, 1995

[30] Foreign Application Priority Data

Jun. 30, 1994 [DE] Germany .......................... 44 22 672.1

[51] Int. Cl.⁶ ............................. C07F 9/02; C07F 15/00
[52] U.S. Cl. ..................... 556/18; 556/21; 556/136; 568/17
[58] Field of Search .......................... 556/21, 18; 568/17

[56] References Cited

U.S. PATENT DOCUMENTS 5,171,892   12/1992   Burk et al. .............................. 568/12

FOREIGN PATENT DOCUMENTS

0398132A2   11/1990   European Pat. Off. .
0643065A1    3/1995   European Pat. Off. .

OTHER PUBLICATIONS

H. Jendralla, et al., "Efficient Synthesis of (R)–and (S)–(6, 6'–Difluorobiphenyl–2,2'–diyl) bis(diphenylphosphine); Electron–Poor Biphenyl–Type Ligands for Transition Metal Catalysts," Tetrahedron: Asymmetry, vol. 5:7, pp. 1297–1320 (1994).

Zassinovich et al., "Asymmetric Hydrogen Transfer Reactions Promoted by Homogeneous Transition Metal Catalysts", Chemical Reviews, 92(5):1051–1069 (1992).

Uehara et al., Journal of Organometallic Chemistry, vol. 239, pp. 1–10 1982.

Primary Examiner—Porfirio Nazario-Gonzalez
Attorney, Agent, or Firm—Finnegan, Henderson, Farabow, Garrett & Dunner, L.L.P.

[57] ABSTRACT

Compounds of the formula I

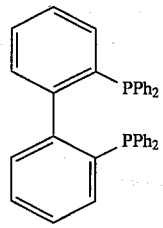

I in which the phenyl rings of the biphenyl molecule can be substituted with up to 8 fluorine and/or chlorine atoms are suitable as catalysts.

14 Claims, No Drawings

HALOGENATED BIPHENYL-2,2'-DIYLBISDIPHENYLPHOSPHINES, THEIR PREPARATION AND THEIR USE

DESCRIPTION

The present invention relates to halogenated biphenyl-2,2'-diylbisdiphenylphosphines, to their preparation and to their use.

Mono- and diphosphines are of considerable importance as ligands in transition metal-catalyzed organic reactions. In recent years, homochiral mono- and diphosphines in particular have found great interest as ligands in transition metal-catalyzed enantioselective reactions, for example in rhodium (I)-, ruthenium(II)- and iridium(I)-catalyzed asymmetric hydrogenations of prochiral alkenes, ketones and imines, in palladium-catalyzed nucleophilic allylic substitutions and Heck coupling reactions, in rhodium(I)-catalyzed hydrosilylations, hydrobortions and hydroformylations of prochiral alkenes and hydrosilylations of ketones and imines, and also in rhodium(I)-catalyzed asymmetric isomerizations of allylamines to the corresponding enamines.

It is evident that, in the known applications of achiral phosphines in transition metal-catalyzed reactions and in all of the abovementioned examples of the application of homochiral phosphines in asymmetric catalytic synthesis (Zassinovich et al., S. Chem. Rev. 1992, 92, 1051–1069) and in tables of around 200 different homochiral phosphines, phosphinites and amidophosphines which have been tested in asymmetric synthesis, all of the phosphines employed are electron-rich. The abovementioned phosphines have the disadvantage that the progress of some reactions catalyzed with the aid of these compounds is poor, inadequate enantioselectivity being a particular drawback.

Surprisingly it has now been found that certain electron-deficient systems, such as halogenated biphenyl-2,2'-diyl-biediphenylphosphines, are in some transition metal-catalyzed reactions superior to the conventional electron-rich mono- and diphosphines with respect to reaction yield obtained, catalytic activity and/or enantioselectivity.

The present invention relates accordingly to compounds of the formula I

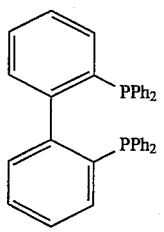

I in which the phenyl rings of the biphenyl molecule are substituted with up to 8 fluorine and/or chlorine atoms. Preference is given to compounds of the formula I in which the phenyl rings are substituted by up to six fluorine and/or chlorine atoms; particular preference to those with up to four fluorine and/or chlorine atoms and especial preference to those having up to two fluorine and/or chlorine atoms. A position of very particular importance is held by the compounds of the formula II.

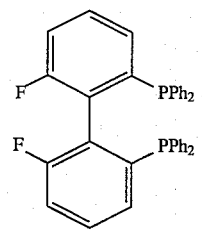

II

The present invention relates to the abovementioned compounds in both the racemic and the chiral form, as the following formulae—which show compounds bearing very particular preference—are intended, by way of example, to cover.

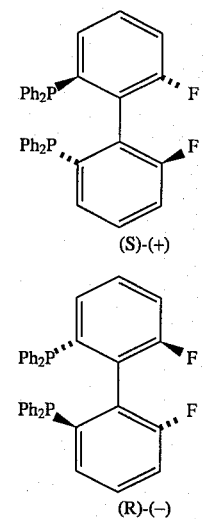

(S)-(+)

(R)-(−)

The present invention also relates to the process for the preparation of compounds of the formulae I and II, which comprises reacting a compound of the formula 4

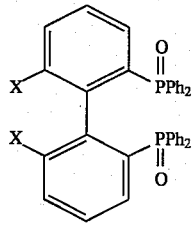

4 in which X is F or Cl, preferably F, with $Cl_2Si(CH_3)H$, $NBu_3$, in an organic solvent, preferably xylene, under an inert gas, preferably nitrogen, or alternatively boiling the compound of the formula 4 under reflux with $HSiCl_3$ and $NBu_3$ in an organic solvent, preferably xylene, to give the compound of the formula I or II, where the phenyl rings of the biphenyl molecule may be substituted with up to 6 additional fluorine and/or chlorine atoms.

The compounds of the formula 4, which occur as important intermediates, in chiral and racemic form are a further subject of the present invention, as is the process for the preparation of compounds of the formula 4, which comprises heating a compound of the formula 3

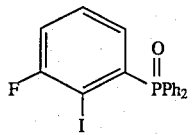

3 in an inert solvent, preferably DMF, with the addition of a transition metal, preferably Cu, where the compound of the formula 3 can be substituted in position 4, 5 and/or 6 with up to 3 fluorine and/or chlorine atoms.

Yet another subject of the present invention is the process for the preparation of the compound of the formula 3, which comprises reacting a compound of the formula 2

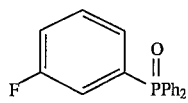
                                                                2 with lithium diisopropylamide in an inert solvent, preferably in THF, and then with iodine, where the compounds of the formulae 2 and 3 may be substituted in position 4, 5 and/or 6 with up to 3 fluorine and/or chlorine atoms.

The present invention additionally relates to a process for the preparation of the compound of the formula 2, which comprises reacting a compound of the formula 1

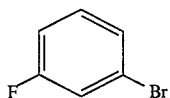
                                                                1 with n-butyllithium in an organic solvent, preferably diisopropyl ether, then with Ph$_2$PCl and subsequently with H$_2$O$_2$ in an alcohol, preferably methanol, where the compounds of the formulae 1 and 2 can be substituted in position 4, 5 and/or 6 with up to three fluorine and/or chlorine atoms.

A process for the preparation of compounds according to the invention is illustrated below in the form of a diagram in which preferred parameters are given.

Diagram 1

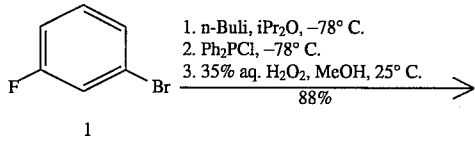

-continued
Diagram 1

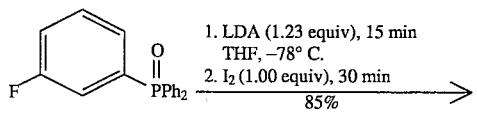

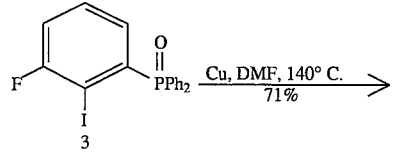

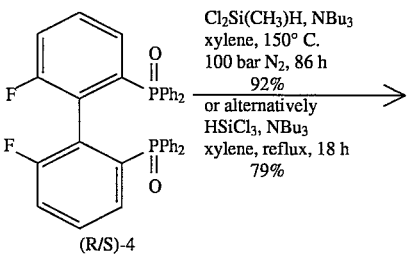

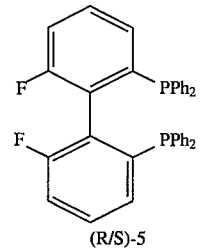

(R/S)-5

The processes mentioned above relate to the racemic compounds. The individual chiral forms of the compounds mentioned can be obtained by customary methods for resolving racemates. A preferred resolution method is illustrated by the diagram which follows. The subsequent explanation of features according to the invention uses the numbering of the compounds from diagram 2.

Diagram 2
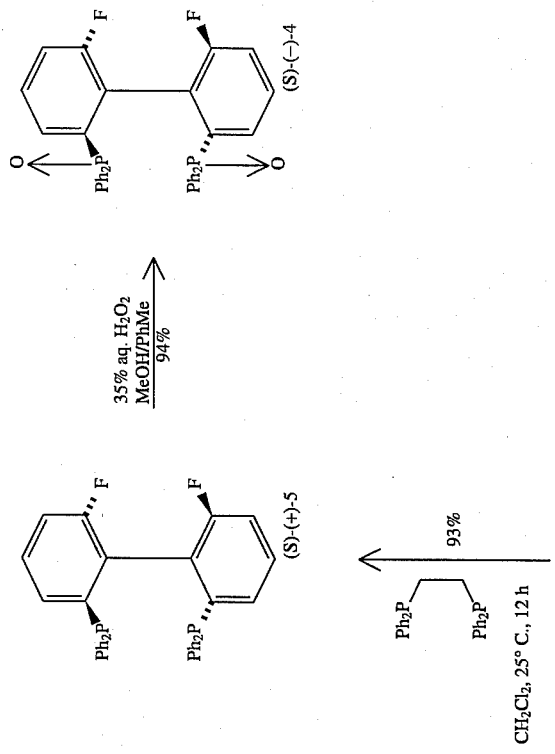

-continued
Diagram 2
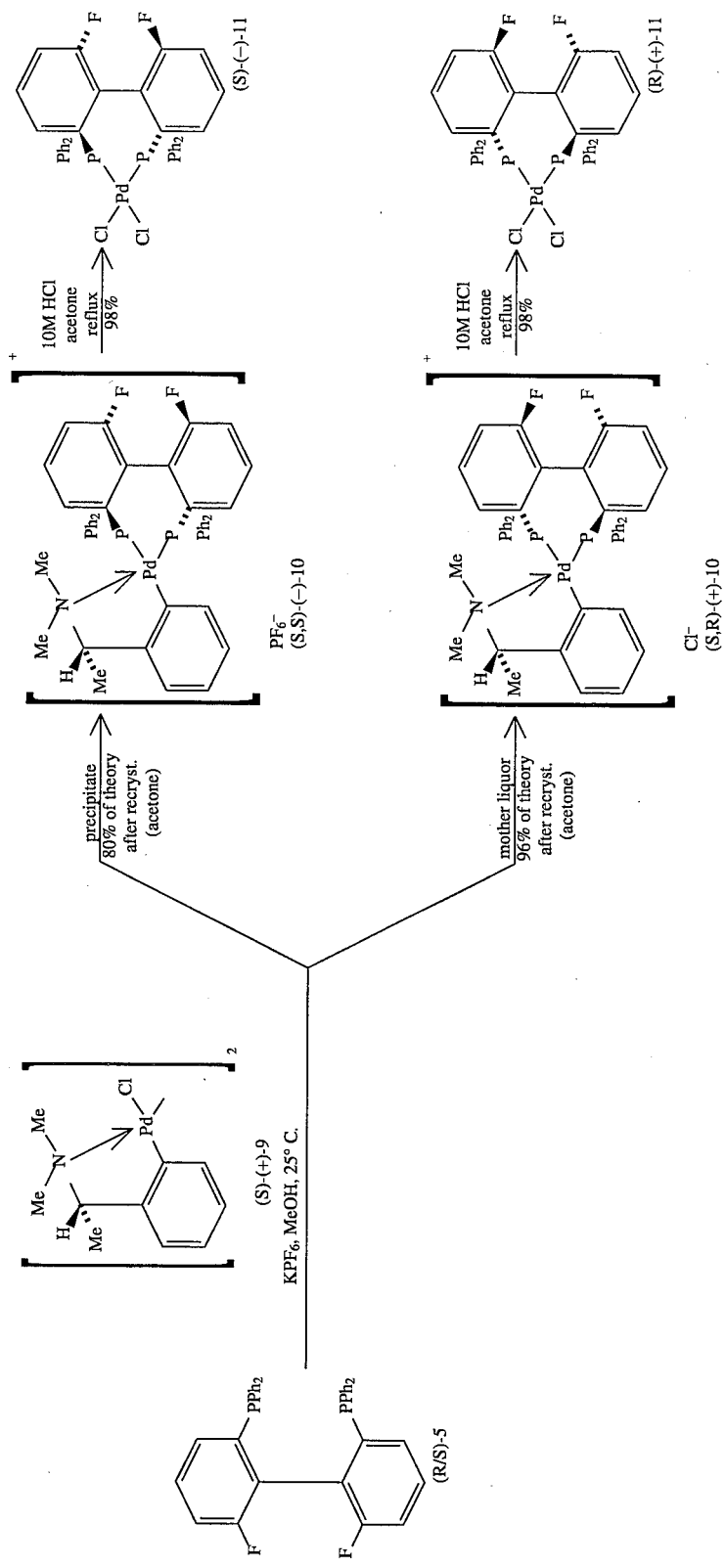

-continued
Diagram 2
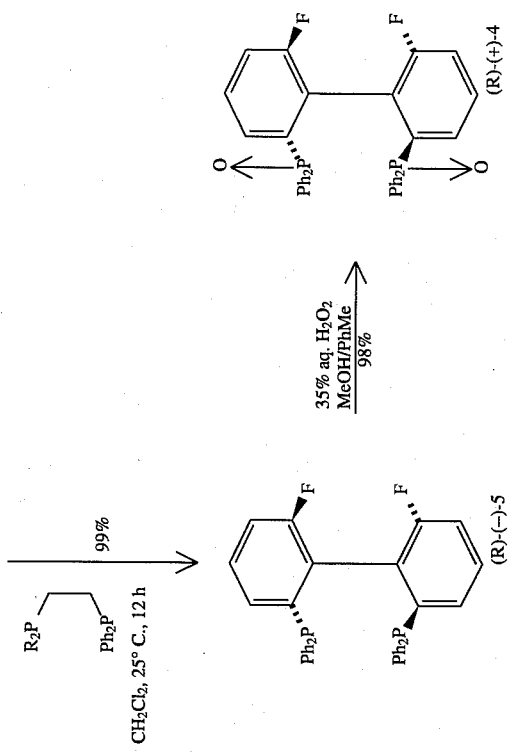

The racemate cleavage of (R/S)-5 to (S)-(+)-5 gives 75% of the theoretical yield, while that to (R)-(-)-5 gives 95% of the theoretical yield. Absolute determination of the optical purity is made by chiral phase HPLC analysis of the corresponding bis(phosphine oxides) (S)-(-)-4 and (R)-(+)-4. The absolute configuration is confirmed by monocrystal X-ray structural analysis of (S,S)-(-)-10.

Further subjects of the present invention are the Rh(I), Ru(II), Pd(II) and PD(O) complexes of the compounds of the formula I.

Their preparation, by reaction of compounds of the formula I or II with suitable complexes of these metals having readily displaceable ligands, is likewise a subject of this invention.

Among such readily displaceable ligands, preference is given to Z,Z-1,5-cyclooctadiene (COD), norbonadiene (NBD) or acetylacetonate (acac). The corresponding transition metal complexes are commercially available or can readily be prepared in a known manner. In the examples of this application (see asymmetric hydrogenation and asymmetric hydroboration/oxidation) there are concrete instructions for this procedure.

The homochiral palladium dichloride complexes with compounds of the formula I or II can also be obtained, as shown in diagram 2, by HCl-induced elimination of the N,N-dimethyl-alpha-phenylethylamine ligand from the diastereomeric palladium complexes of the formula 10.

Yet another subject of the present invention is the use of the compounds according to the invention as catalysts. The catalysts of the invention are particularly suitable for catalyzing organic addition, substitution, rearrangement and coupling reactions. The optically pure diphosphines 5 and their palladium dichloride complexes 11 are of unusually good thermal and chemical stability. For example, it has not hitherto been possible to carry out the thermal racemization of solutions of homochiral 5. Even after heating a solution of (S)-(+)-5 in tetralin under reflux (b.p. 207° C.) for 2.5 hours in a argon atmosphere, the specific rotation is unchanged and chiral phase HPLC analysis of the corresponding phosphine oxide 4 still shows 100% ee. The enantiomers of 11 (m.p. 310°–312° C.) are recovered in unchanged form after stirring for 16 hours in a solution of excess potassium cyanide in water/methanol/dichloromethane. There is no cleavage to give the free diphosphine and potassium tetracyanopalladate. The extremely high thermal configurational stability of the homochiral diphosphine 5, and the high thermal and chemical stability of its transition metal complexes (for example 11), are an essential basis for the extraordinarily broad scope for application of the latter as catalysts of organic reactions. The unusually high resistance to thermal racemization guarantees that complete optical induction of corresponding catalysts is obtained even at high reaction temperatures. In principle, the high chemical resistance enables the catalyst to be employed in the presence of particularly aggressive reagents.

In the text below, the advantages of the generally employable catalysts are illustrated with reference t concrete, particularly preferred examples. The specifi rotation of, for example, the optically pure diphosphin (S)-(+)-5 (compound of the formula II) varies dramatically in different solvents (Table 1). For example, th direction of the optical rotation, of +114.9° to -73.0° is reversed if tetralin is used instead of toluene a solvent. The significance of this hitherto unknow phenomenon for the asymmetric catalysis brough about corresponding transition metal complexes has not yet be clarified. This circumstance makes it possible to exe a strong and targeted influence on the optical induction by variation of the solvent, and to prepare the reactio product in both absolute configurations using the sa catalyst, depending on the particular solvent that used.

TABLE 1

Specific rotation $[\alpha]_D^{25}$ of (S)-(+)-5 measured in different solvents.

| $[\alpha]_D^{25}$, (S)-(+)-5 | c | Solvent |
|---|---|---|
| +153.3 | 1.02 | THF |
| +145.3 | 0.47 | Dioxane |
| +123.7 | 1.03 | Dichloromethane |
| +114.9 | 0.99 | Toluene |
| +95.5 | 0.73 | Mesitylene |
| +46.7 | 1.04 | Chloroform |
| +21.4 | 0.64 | o-Xylene |
| -73.9 | 0.46 | Tetralin |

The rhodium(I) complex of (R)-(-)-5 has a high cataly activity and enantioselectivity with regard, for examp to the hydroboration of prochiral olefins. The hydrobo tion of p-methoxystyrene 12 with 2 equivalents catecholborane in THF at 0° C. in the presence of 2 mol % of a catalyst formed in situ from (1,5-cyclooctadiene) (2,4-pentanedionato)rhodium(I) and (R)-(-)-5 is quantitative within 1.5 h. Oxidation with excess hydrogen peroxide at 25° C. gives 78% of the Markovnikov product 1-(4-methoxyphenyl)ethanol 13 [77.8% ee of the (R) configuration] and 22% of the anti-Markovnikov product 4-methoxyphenethyl alcohol 14 (diagram 3). The presence of the rhodium(I) complex of the electron-deficient homochiral diphosphine 5 thus brings about a drastic reduction in the activation energy of hydroboration, reverses the anti-Markovnikov selectivity of the hydroboration to provide for Markovnikov selectivity, and gives the product alcohol, even at a reaction temperature of 0° C. which can readily be implemented in industry, in a substantially higher optical purity than that given by electron-rich diphosphines at from +70° to -20° C. At 0°-25° C., electron-rich diphosphines no longer give any significant induction.

Diagram 3:

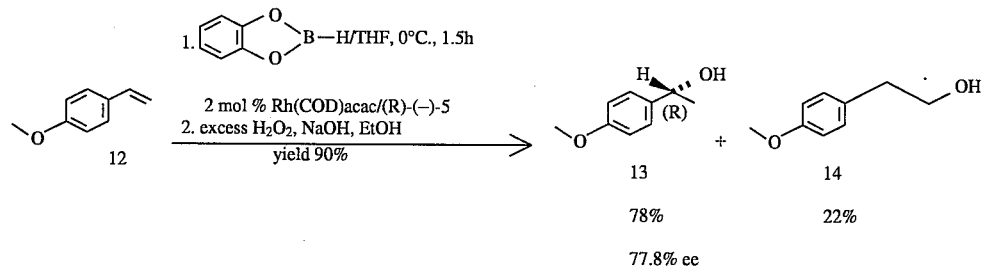

The rhodium(I) complex of (R)-(–)-5 catalyzes the addition of hydrogen onto C=C double bonds under a high hydrogen pressure.

2-Benzylidenesuccinic acid 4-[(4-BOC-amino)-1-piperidide] 37 at 25° C. under 1 bar of hydrogen in the presence of 1 mol % of the catalyst formed in situ from di-μ-chlorobis(cycloocta-1c,5c-diene)rhodium(I) and (R)-(–)-5 is not hydrogenated. Under a high hydrogen pressure, an in situ Rh(I) complex of the homochiral diphosphine (R)-(–)-5 brings about asymmetric hydrogenation (see the examples).

The palladium complexes of (R/S)-5 with palladium chloride or palladium acetate give better yields than corresponding palladium complexes of electron-rich mono- or diphosphines with regard to aryl-aryl couplings of arylboronic esters with arylhalides in an aqueous/organic two-phase mixture (Suzuki coupling). Similarly, they give better yields in aryl-vinyl couplings of the Heck type. The palladium catalysts (S,S)-(–)-10, (S,R)-(+)-10, (S)-(–)-11 and (R)-(+)-11 give superior chemical and optical yields in asymmetric allylic substitution reactions, Heck couplings and cyclization reactions.

EXAMPLES

Reagents, equipment and general methods: acetone (99.5%, Riedel-de Haën), 1,2-bis(diphenylphosphino)ethane (99%, Aldrich), 1-bromo-3-fluorobenzene (>99%, Aldrich). n-butyllithium (15% strength solution in hexanes, 1.6 N, Chemetall Gesellschaft), (–)-(2R, 3R)-2,3-O,O'-dibenzoyltartaric acid and its (+)-(2S,3S) enantiomer (>99%, Fluka), catecholborane (1.0 N solution in THF, Aldrich), (1,5-cyclooctadiene) (2,4-pentanedionato)rhodium(I) (99%, Aldrich), di-μ-chlorobis[(cycloocta-1c,5c-dienerhodium(I)], (S)-(+)-di-μ-chlorobis {2-[1-(dimethylamino)ethyl]phenyl-C,N}dipalladium (9) (98%, Aldrich), dichloromethane (99.8%, Riedel-de Haën), dichloromethylsilane $Cl_2Si(CH_3)H$ (97%, Janssen), diethyl ether (>99%, Hoechst), hydrogen peroxide (35% aqueous solution, Riedel-de haën), iodene (99.8%, Riedel-de Haën), mesitylene (99%, Fluka), methanol (99.5%, 0.2% $H_2O$, Riedel-de Haën), potassium hexafluorophosphate (>99%, <0.03% $H_2O$, aldrich), tri-n-butylamine (98%, Merck-Schuchardt), trichlorosilane (99%, Aldrich), o-xylene (99.5%, Riedel-de Haën) were employed as bought.

Chlorodiphenylphosphine $ClPPh_2$ (technical grade, 95%, Aldrich) (boiling point 98°–100° C./0.2 torr) and p-methoxy-styrene (97%, Aldrich) (boiling point 41°–42° C./0.5 torr) were distilled in vacuo directly before use. Diisopropylamine (99%, Aldrich) and diisopropyl ether (>99%, Hoechst) were distilled from calcium hydride in an argon atmosphere directly before use (Karl-Fischer titration gave <0.01% $H_2O$ in $iPr_2O$ and ≦0.05% $H_2O$ in $iPr_2NH$). N,N-dimethylformamide (DMF) was left to stand for several days in a sealed flask over activated 4A molecular sieves and was then distilled in vacuo. Tetrahydrofuran (THF) was dried directly before use by passing it through ICN aluminum oxide B (activity 1, 1 g/3 ml THF) (Karl-Fischer titration gave <0.01% $H_2O$).

Copper powder (99.8%, Riedel-de Haën) was activated by the following method: 260 g of copper powder were added to a solution of 52 g of iodine in 2.6 l of acetone and the mixture was stirred for 10 min. The copper was filtered through a Büchner funnel and stirred for 10 min in a solution of 650 ml of concentrated hydrochloric acid in 650 ml of acetone. The copper powder was filtered off, washed with 3×200 ml of acetone and dried under vacuum in a desiccator.

All reactions were carried out in dry glass apparatus under an argon atmosphere.

The melting points (m.p.) were determined using a Büchner capillary melting point instrument (in accordance with Dr. Tottoli) and are uncorrected. HPLC: Kontron 420 Pump with Kontron 425 Gradient unit, Kontron 360 Autosampler (20 μl Injection Loop), Kontron 432 HPLC UV detector and Kontron 450-MT2 data processing system, or alternatively Spectra Physics SP 4200 Pump/8750 Organizer (10 μl Injection Loop) with SP 8700 Solvent Metering Systems, Spectra 100 UV-Vis Detector and SP 4100 Computing Integrator. TLC: glass plates precoated with silica gel 60 F-254 (E. Merck) measuring 5×10 cm; detection of the spots with Universal UV lamp Camag (254 nm). Ultrasonic cleaning bath: Elma Transconic TS540.

$^1$H-NMR (internal standard TMS): Varian Gemini 200 (200 MHz), Bruker AM 400 (400 MHz) and Bruker ARX 500 (500 MHz). $^{13}$C-NMR (internal standard TMS): Bruker AM 270 (67.93 MHz) and Bruker ARX 500 (125.77 MHz). $^{19}$F-NMR (internal standard fluorotrichloromethane): Bruker AC 100 (94.2 MHz), Varian Gemini 200 (188.14 MHz), Bruker AM 400 (376.50 MHz) and Bruker ARX 500 (470.59 MHz). $^{31}$P-NMR (external standard 80% aqueous phosphoric acid): Bruker AM 270 (109.35 MHz), Bruker AM 360 (145.79 MHz) and Bruker ARX 500 (202.46 MHz). The δ and J values indicated for all compounds with the exception of (R/S)-4, (S)-(–)-4 and (R)-(+)-4 correspond to conventional first-order analysis of the spectra. All of the NMR spectra of (R/S)-4, (S)-(–)-4 and (R)-(+)-4 were subjected to complete analysis using decoupling techniques and $^1$H-$^{13}$C-NMR correlation (hsqc). IR: Perkin Elmer 683 Spectrometer. MS: a) fast atom bombardment positive ionization (+FAB): VG ZAB SEQ; NBA indicates p-nitrobenzyl alcohol. b) dissociation chemical ionization (DCI): Kratos MS 80. c) positive eletrospray ionization (+ESI): VG BIO-Q; acetonitrile/water (1:1)+0.5% formic acid. The optical rotation was determined on a Perkin-Elmer 241 polarimeter using a microcuvette of 10 cm in length.

The X-ray structures were determined on monocrystals sealed in Lindemann glass capillaries, using a computer-controlled quadrilateral diffractometer (R3m/V, Siemens). 25 reflections with θ>4° (for 4 and S,S-10) or θ>8° (for 7) were used to determine the cell dimensions. The phase problem was solved by the direct method[54], minimization of $\Sigma w(Fo^2-Fc^2)^2$[55], weighting scheme w in accordance with the numerical statistics.

(3-Fluorophenyl)diphenylphosphine oxide (2)

A 1.6 N solution of n-butyllithium in hexanes (1060 ml, 1.7 mol) was added over the course of 30 min at −78° C. via a flexible needle to a solution of 1-bromo-3-fluorobenzene (1-bromo-3-fluorobenzene (1) (298.7 g, 1.7 mol) in diisopropyl ether (4.0 l). The yellow suspension was stirred for a further hour at −78° C. Chlorodiphenylphosphine (394 g, 1.78 mol) was added dropwise over the course of 20 min at from −78° C. to −60° C. The yellow solution was left to warm to 0° C. over the course of 2 h, during which it gradually became a white suspension. Saturated aqueous ammonium chloride solution (1.0 l) was added dropwise. The organic layer was separated off, washed with brine (2×700 ml), dried over $MgSO_4$ and then filtered. The solvent was evaporated under vacuum and the oily residue was dried under a high vacuum until crystallization began, to give a pale yellow semi-solid substance (479 g, 1.71 mol, yield 100%). This crude produce was oxidized without purification to give phosphine oxide. An analytical sample was obtained by washing the crude product with methanol to give colorless crystals of (3-fluorophenyl-diphenylphosphine, m.m. 59°–61° C., $R_f$ 0.26 (cyclohexane) [$R_f$ of 1: 0.73], $^1$H-NMR (200 MHz, CDCl$_3$): δ6.84–7.17 (m, 3H), 7.20–7.60 (m, 11H); MS (DCI, CH$_3$OH): m/e (rel. intensity) 281 (M+H, 100), 280 (M, 83), 203 (M-C$_6$H$_5$,24); IR (KBr): 3070, 1602, 1580, 1475, 1437, 1415, 1216, 876, 791, 742, 694, 685 cm$^{-1}$.

35% strength aqueous hydrogen peroxide (183 ml, 2.1 mol) was added dropwise at <40° C. to a suspension of the phosphine (476.5 g, 1.7 mol) in methanol (2.1 l). After the clear yellow solution obtained had been stirred for 10 min at 20° C., TLC indicated a quantitative reaction (ethyl acetate/isopropanol 20:1; $R_f$ 2: 0.44; phosphine: 0.75). A saturated aqueous solution of sodium sulfite (640 ml) and 1 N hydrochloric acid (300 ml) was added, and the mixture was stirred until a test with iodine starch paper indicated the complete reduction of the excess hydrogen peroxide. Methanol was evaporated under vacuum, and dichloromethane (4.0 l) was added with stirring. The organic layer was separated off and washed with 2×1 l of saturated sodium bicarbonate solution and with 2×1 l of water. The organic phase was dried (MgSO$_4$) and the solvent was evaporated under vacuum to leave a white powder (475 g). This powder was triturated with diisopropyl ether (900 ml) in an ultrasonic cleaning bath, the mixture was filtered, and the solid was washed again with diisopropyl ether (300 ml) and dried under vacuum: 441 g (1.49 mol, 88% yield based on 1), m.p. 143°–145° C. HPLC [250×4.6 mm Lichrosorb RP 18 7 μm, 1 ml/min (630 ml) CH$_3$CN+370 ml H$_2$O+0.1% NH$_4$OAc), detection: 254 nm, $t_{ret}$ 8.50 min] gave a purity of 98.1%. $^1$H-NMR (200 MHz, CDCl$_3$): θ7.18–7.80 (m); MS (DCI, CH$_3$OH): m/e (rel. intensity 297 (M+H, 100) 296 (M, 11), 295 (M–H, 13); IR (KBr): 3055, 1583, 1440, 1228, 1188, 1122, 1110, 725, 708, 700, 690, 542, 511 cm$^{-1}$.

(3-Fluoro-2-iodophenyl)diphenylphosphine oxide (3)

Note: it is absolutely necessary in this step to use carefully dried glass apparatus, THF and diisopropylamine and to avoid an excess of iodine. Even the presence of the 0.2% H$_2$O present in commercial diisopropylamine had an adverse effect on the results (in each case 10–15% of 2 and diiodide 6 were not reacted).

A 1.6 N solution of n-butyllithium in hexanes (769 ml, 1.23 mol) was added at –70° C. to a solution of diisopropylamine (176 ml, 1.24 mol) in THF (1.0 ). The solution was allowed to warm up to –20° C., and was then cooled again to –70° C. This clear yellow LDA solution was added over the course of 25 min at –70° C. with a flexible needle to a cold (–78° C.) suspension of 2 (296.3 g, 1.0 mol) in THF (2.0 l). The mixture was stirred at –78° C. for 15 min to give an orange-red suspension. A solution of iodine (254 g, 1.0 mol) in THF (1.0 ) was added dropwise over 30 min. at ≦–70° C., to give a thick yellow-orange suspension. This suspension was allowed to warm up to 0° C. over the course of 1.5 h. A solution of sodium thiosulfate (74 g) in water (600 ml) was added followed by the addition of brine (1.2 l). The organic phase was separated off and washed with 3×1.2 l of brine. It was dried (MgSO$_4$) and the solvent was evaporated under vacuum. The residue was triturated with diisopropyl ether (1.0 l) in an ultrasonic cleaning bath (≈1 min.). The solids were filtered off and dried under vacuum to give a colorless powder (358 g, 848 mmol, 85% yield), m.p. 155°–157° C. HPLC [250×4.6 mm Lichrosorb RP18 7 μm, 1.5 ml/min (630 ml CH$_3$CN+370 ml H$_2$O+0.1% NH$_4$OAc), detection: 220 nm] gave 0.6% of 2 ($t_{ret}$ 4.41 min), 97.8% of 3 ($t_{ret}$ 4.71 min), 1.6% of 6 ($t_{ret}$ 7.47 min). $^1$H-NMR (200 MHz, CDCl$_3$): δ697 (ddd, $^3J_{H,P}$=13 Hz, $^3J_{H,H}$=7 Hz, $^4J_{H,H}$=1 Hz, 1H), 7.15–7.38 (m,2H), 7.40–7.80 (m, 10H); $^{19}$F{$^1$H}-NMR (94.2 MHz), CDCl$_3$): δ –87.3 (d, $^4J_{F,P}$=6.8 Hz); $^{19}$F-NMR (94.2 MHz, CDCl$_3$): δ –87.3 (td, $^4J_{F,P}$=$^3J_{F,H}$=7.0 Hz, $^4J_{F,H}$=5.2 Hz); MS (DCI): m/e (rel. intensity) 423 (M+H, 100); IR (KBr): 2920(w), 1437, 1400, 1244, 1182, 1117, 791, 718, 697, 542, 520 cm$^{-1}$.

In the products from test reactions, which [owing to traces of water in he reagents and an excess of iodine (1.13 equivalents)] contained up to 15% of diiodide 6, the characteristic spectral signals were observed: $^1$H-NMR (200 MHz, CDCl$_3$): δ6.68 (dd, $^3J_{H,P}$=12.5 Hz, $^3J_{H,H}$=9 Hz); $^{19}$F{$^1$H}-NMR (94.2 MHz, CDCl$_3$): δ –65.8 (d, $^4J_{F,P}$=5.9 Hz); $^{19}$F-NMR (94.2 MHz, CDCl$_3$): δ –65.8 (≈t, $^4J_{F,P}$=5.9 Hz, $^4J_{F,H}$=5.7 Hz); MS (+ESI): m/e 549 (M+H).

(RS)-(6,6'-Difluorobiphenyl-2,2'-diyl)bis(diphenylphosphine oxide) ((R/S)-4)

A mixture of 3 (350 g, 829 mmol), activated copper powder (163 g, 2.56 mol, cf. reagents and equipment) and DMF (1.7 l) was stirred at 140° C. (oil bath temperature) for 1.5 h. The mixture was cooled to ambient temperature and the solvent was evaporated to dryness under vacuum at 70° C. The residue was extracted by repeated stirring with hot dichloromethane (4×2 l). The filtered extracts were combined and evaporated to dryness, and the residue was dried under a high vacuum to give a solid (223 g, yield 91%) which according to HPLC [conditions as described for 3] consisted of 92% of 4 ($t_{ret}$ 7.25 min) and 8% of 2 (<0.1% of 3). Ultrasound treatment in dichloromethane (1.3 l) for 1 min gave a colorless solid (173 g, yield 71%), m.p. 280°–282° C., >99.5% of 4. An analytical sample was obtained by recrystallization, crystals being obtained by boiling under reflux from dichloromethane/ethyl acetate (3:1), m.p. 283°–284° C. NMR spectra were identical with those of the optically pure compounds (S)-(–)-4 and (R)-(+)-4 (see below). MS (+FAB, MeOH/NBA): m/e (rel. intensity): 591 (M+H, 100) 13 (M–Ph, 7), 389 (M–Ph$_2$PO, 17), 201 (Ph$_2$PO, 27); IR (KBr): 3058 (w), 1436, 1422, 1240, 1206, 1192, 1117, 742, 695, 566, 532 cm$^{-1}$.

Crystals suitable for the X-ray analysis were obtained by recrystallization from boiling toluene. Crystal of 0.31×0.18× 0.17 mm$^3$; cell dimensions: a=26.570(4), b=12.840(4), c=20.296(3)Å, β=120.04 (1)°; C2/c,z=8, $D_x$ =1.309 mg/m$^3$; λ(Mo K$_α$)=0.7107 Å, θ$_{max}$=25.06°, 5107 individual reflections, 3117 with (Fo) >4σ; 379 parameters, wR2=0.154 (all reflections), R1=0.046 (3117 reflections), S=0.92, maximum and minimum in the differential Fourier synthesis: 0.46, –0.39 e/Å$^3$.

(RS)-(6,6'-Difluoro-5-iodobiphenyl-2,2'-diyl)bis(diphenylphosphine oxide) (7)

The reaction of monoiodide 3, which contains 14% diiodide 6, under the same Ullmann coupling conditions gave a product consisting of 89% of 4, 10% of 7 and 1% of an unidentified constituent. 31.5 g of this mixture were chromatographed on 3 kg of RP18 silica gel (eluent: methanol/water 1:1) and, following recrystallization from hot dichloromethane/ethyl acetate (3:1), gave 2.7 g of 7, colorless needles, m.p. 272°–274° C., HPLC (conditions as described for 3, $t_{ret}$ 11.68 min): >99%. $^1$H-NMR (500 MHz, CDCl$_3$): δ6.78 (dd, $^3J_{H,P}$=13.0 Hz, $^3J_{H,H}$=8.4 Hz, 1H), 7.06 (ddd, $^3J_{H,P}$=13.0 Hz, $^3J_{H,H}$8.0 Hz, $^4J_{H,H}$=1.2 Hz, 1H), 7.12 (br t, $^3J_{H,P}$=$^3J_{H,H}$=8.5 Hz, 1H), 7.30–7.36 (m, 5H), 7.40–7.48 (m, 6H), 7.50–7.56 (m, 2H), 7.58–7.68 (m, 8H), 7.70 (ddd, 1H); $^{15}$F{$^1$H}-NMR (94.2 MHz, CDCl$_3$): δ–89.6 (dt, $^4J_{F,F}$=6.3 Hz, $^5J_{F,P}$=0.9 Hz, $^5J_{F,P}$=0.9 Hz), –110.3 (dt, $^4J_{F,F}$=6.9 Hz, $^5J_{F,P}$=08 Hz, $^5J_{F,F}$=0.9 Hz); $^{19}$F-NMR (94.2 MHz, CDCl$_3$): δ–89.6 (br t, $^4J_{F,H}$=6.3 Hz), –110.3 (br qua, $^4J_{F,P}$=$^3J_{F,H}$=$^4J_{F,H}$=7.0 Hz); $^{31}$P{$^1$H}-NMR (109.35 MHz, CDCl$_3$): δ+28.47 (d, $^4J_{P,F}$=6.3 Hz), +28.58 (d, $^4J_{P,F}$=6.9 Hz); MS (DCI, MeOH): m/e (rel. intensity) 717 (m+H, 85), 515 (M–Ph$_2$PO); IR (KBr): 3057 (w), 1438, 1393, 1203, 1118, 705, 695, 533 cm$^{-1}$. a baseline separation of the enantiomers of 7 [t$_{ret}$ 20.34 (+)-isomer and 22.14 min (–)-isomer] was obtained on a 250×4.6 mm DNBPG-Baker bond column using the eluent n-heptane/ethanol 15:1.

Crystals suitable for the X-ray analysis were obtained by recrystallization from boiling dichloromethane. Crystal 0.45×0.45×0.3 mm$^3$; cell dimensions: a=10.462(1), b=14.579(1), c=20.467(2) Å; P2$_1$2$_1$2$_1$, Z=4, D$_x$=1.524 mg/m$^3$; λ(MoK$_α$)=0.7107 Å, θ$_{max}$=28.06°, 7569 individual reflections, 7063 with (Fo)>4σ; 488 parameters, wR2=0.065 (all reflections), R1=0.023 (7063 reflections), S=0.67, maximum and minimum in the differential Fourier Synthesis: 0.53, –0.26 e/Å$^3$.

Experiment on the resolution of (R,S)-4 with (–)-(2R,3R)-2,3-O,O'-dibenzoyltartaric acid a) A solution of (2R,3R)-(–)-di-O-benzoyltartaric acid (951 mg, 2.53 mmol) in ethyl acetate (6 ml) was added to a solution of (R/S)-4 (815 mg, 1.38 mmol) in boiling dichloromethane (15 ml). The solution was boiled under reflex for 3 h. No precipitate formed. The solution was left to stand overnight at 20° C. No precipitate formed. b) (2S,3S)-(+)-Di-O-benzoyltartaric acid monohydrate (1.70 g, 4.50 mmol) and (R/S)-4 (2.00 g, 3.35 mmol) were dissolved in dichloromthane (30 ml). n-Heptane (13 ml) was added dropwise with stirring. The turbid mixture was left to stand for 30 min, and two layers formed. The layers were separated and were both washed, independently of one another, with 2 N sodium hydroxide (2×15 ml) and with water (2×15 ml). The organic solutions were dried (MgSO$_4$) and the solvents were evaporated under vacuum. Top layer: colorless solid (0.98 g.), (R/S)-4 (<1% ee) according to the optical rotation (365 nm, c=0.56, CH$_3$OH) and HPLC of the chiral phase. Bottom layer: colorless solid (0.75 g), (R/S)-4 (<1% ee) according to the optical rotation and HPLC of the chiral phase.

(R)-(6,6-Difluorobiphenyl-2,2'diyl)bis(diphenylphosphine) ((R/S)-5)

a) By reduction of (RS)-4 with trichlorosilane: Tri-n-butylamine (150 ml, 638 mmol) and trichlorosilane (43 ml, 426 mmol) were added to a suspension of (R/S)-4 (64.3 g, 109 mmol) in deoxygenated xylene (900 ml). The suspension was heated to reflux (138° C.) to give a clear solution. This solution was maintained at gentle reflux for 18 h. After a reacting time of 9 h, additional tri-n-butylamine (150 ml, 638 mmol) and trichlorosilane (10 ml, 99 mmol) were added. TLC (EtOAc/MeOH 19:1) indicated a quantitative reaction of 4 (R$_f$ 0.03) to 5 (R$_f$ 0.86) and a small quantity of monooxide (R$_f$ 0.77). The reaction mixture was cooled to 0° C. Deoxygenated 30% strength aqueous sodium hydroxide solution (400 ml) and dichloromethane (500 ml) were added, and the mixture was stirred at 60° C. until the organic and the aqueous layer became clear (30 min). The aqueous layer was removed using a cannula and the organic layer was washed with deoxygenated 30% strength aqueous sodium hydroxide solution (400 ml), water (3×400 ml) and brine (400 ml), dried (MgSO$_4$), filtered and evaporated under vacuum. The residue was dried under a high vacuum and then dissolved in dichloromethane (1.1 l), and subsequently cyclohexane (1.1 l) was added. The solution was filtered through a layer (30 cm high) of silica gel (35–70 μm, 850 g) and the layer was washed with dichloromethane/cyclohexane (1:1, 3.0 l). The filtrates were evaporated under vacuum to give a colorless solid (48.0 g, 86.0 mmol, yield 79%), m.p. 215°–217° C., HPLC (250×4.6 mm Nucleosil 120 C8 7 μm, 1 ml/min, 85% acetonitrile/15% water, detection at 254 nm, injection of 10 μl of a solution of 1.0 mg of 5 and 5 ml of CH$_3$CN with ultrasound treatment, t$_{ret}$ 14.50 min) gave a purity of >99%. An analytical sample was obtained by recrystallization from boiling toluene/ethanol (4:5): m.p. 222°–223° C.; $^1$H-NMR (200 MHz, CDCl$_3$) δ6.83–6.98 (m, 4H), 7.10–7.40 (m, 22H); $^{19}$F-NMR (188.14 MHz, CDCl$_3$): δ–112.6 (m); $^{31}$P{$^1$H}-NMR (109.35 MHz, CDCl$_3$): δ–12.70 (t, $^4J_{P,F}$=$^5J_{P,F}$=9.3 Hz); MS (DCI, CHCl$_3$) m/e (rel. intensity) 559 (M+H, 53), 373 M–PPh$_2$, 100); IR (KBr): 3035 (w), 1562, 1446, 1432, 1417, 1234, 790, 742, 693 cm$^{-1}$.

b) By reduction of (R,S)-4 with dichloromethylsilane: (R/S)-4 (13.47 g, 22.8 mmol) was suspended in O-xylene (150 ml) in a cylindrical glass insert for a steel autoclave. Argon was bubbled through the suspension for 10 min. Dichloromethylsilane (11.9 ml, 13.1 g, 114 mmol) was added, followed by tri-n-butylamine (28.4 ml, 22.2 g, 121 mmol). The argon-filled glass insert was placed in the autoclave. Nitrogen (5 bar) was injected, and then the pressure was reduced very slowly. Nitrogen (100 bar) was injected, and the autoclave was heated at an internal temperature of 150° C. for 86 h. The autoclave was cooled to ambient temperature. The nitrogen pressure was then let down and the glass insert was removed. The TLC of an aliquot of the dark-brown reaction mixture, diluted with dichloromethane, indicated the undisturbed formation of 5, the residues of 4 and monooxide being close to the detection limit. All volatile constituents were evaporated (bath 60° C./<20 mbar). Methanol (100 ml) was added to the dark-brown residue, and the suspension was treated for 5 min in an ultrasonic cleaning bath. The solid was filtered, washed with methanol (20 ml) and dried under vacuum to give a crude off-white product (12.8 g, yield 100.5%), m.p. 213°–220° C. Isopropanol (30 ml) was added and the suspension was treated with ultrasound for 1 min. The solid was filtered and dried under vacuum: colorless powder (11.7 g, 21.0 mmol, yield 92%), m.p. 221°–223° C.; spectra identical with those described under a).

c) By reduction of (R/S)-7 with dichloromethylsilane: The reaction of (R/S)-7 (1.14 g, 1.60 mmol), dichloromthylsilane (918 mg, 7.98 mmol) and tri-n-butylamine (1.55 g, 8.46 mmol) in o-xylene (15 ml) under the same conditions as described under b) gave, following the same treatment and subjection to ultrasound in methanol (10 ml), the crude product (90% mg, yield 102%) as an off-white solid, m.p. 213°–219° C. Ultrasound treatment in isopropanol (2 ml) gave a colorless powder (808 mg, 1.45 mmol, yield 91%), m.p. 221°–223° C.; spectra identical to those described under a).

Resolution of (R/S)-5 over palladium complexes 10 {(S)-2-[1-(dimethylamino)ethyl]phenyl-C,N} [(S)-(6,6'-di-fluorobiphenyl-2,2'diyl)bis(diphenylphosphine)]palladium(II) hexafluorophosphate (S,S)-(–)-10

A suspension of (R/S)-5 (4.36 g, 7.38 mmol) and (S)-(+)-di-μ-chlorobis{2-[1-(dimethylamino)ethyl]phenyl-C,N}dipalladium (9) (2.19 g, 3.69 mmol) in deoxygenated methanol (430 ml) was stirred at 25° C. for 2 h until an almost clear, pale yellow solution had formed. A very small quantity of undissolved substances were removed by filtration. A solution of potassium hexafluorophosphate (680 mg, 3.69 mmol) in deoxygenated water (430 ml) was added dropwise. A pale yellow solid was precipitated, and the suspension was stirred for 4 h. The course of the reaction was monitored by TLC (100% isopropanol; R$_f$(R/S)-5: 0.72, (S,S)-10: 0.57, (S,R)-10: 0.37, 9: 0.00). The precipitates were collected by means of filtration, washed with 50% strength deoxygenated aqueous methanol solution (300 ml) and then with diethyl ether (150 ml). [Whereas these washings were discarded, the original filtrate for the isolation of (S,R)-(+)-10 was kept (cf. next paragraph)]. The pale yellow solid was dried under vacuum and gave crude (S,S)-10 (3.33 g, 3.48 mmol, yield 94% of the theoretical value); m.p. 218°–220° C. (decomposition); $[\alpha]^{25}_D$ –198.6° (c=0.967, acetone). $^1$H-NMR signals of its diastereomer (S,R)-10 could not be detected although traces were found by TLC (diastereoselectivity>98:2). The crude complex was dissolved in deoxygenated acetone (40 ml), and diethyl ether (40 ml) was slowly added. The mixture was left to stand in a sealed flask for 8 h. The precipitate was collected by filtration and dried under vacuum: 2.83 g (2.95 mmol, yield 80% of the theoretical value) of a pale yellow solid, m.p. 223°–225° C. (decomposition), $[\alpha]^{25}_D$ –203.2° (c=0.98, acetone): $^1$H-NMR (200 MHz, acetone-d$_6$) δ1.36 (d, J=6.5 Hz, 3H, NCH$_3$), 1.68 (d, J=2.5 Hz, 3H, NCH$_3$), 2.68 (m, ca. t, J=3.7 Hz, 3H, NCH$_3$), 5.54 (qua, J=6.5 Hz, 1H, NCHCH$_3$), 6.32 (≈t, J=7.0 Hz, 1H), 6.58 (≈qua d, J=8.0 and 1.0 Hz, 1H), 6.68–6.86 (m, 4H), 7.06–8.26 (m, 24H); $^{31}$P{$^1$H}-NMR (145.79 MHz, acetone-d$_6$) δ–143.7 (sept. $^1$J$_{P,F}$=707 Hz, PF$_6^-$), +11.5 (dd, $^2$J$_{P,P}$=45 Hz, $^4$J$_{P,F}$=8 Hz), ±35.3 (dd, $^2$J$_{P,P}$=45 Hz, $^4$J$_{P,R}$=7 Hz); $^{19}$F{$^1$H}-NMR (376.50 MHz, acetone-d$_6$, the left-hand side of the PF$_6$ doublette was adjusted to –70 ppm in accordance with literature figures for NaPF$_6$) δ–70.9 (d, $^1$J$_{F,P}$=707 Hz, 6F, PF$_6^-$), –106.2 (ddd, $^4$J$_{F,P}$=7.3 Hz, $^5$J$_{F,F}$=5.9 Hz, $^5$J$_{F,P}$=1.7 Hz), –106.4 (ddd, $^4$J$_{F,P}$=7.7 Hz, $^5$J$_{F,F}$=5.9 Hz, $^5$J$_{F,P}$=1.7 Hz); MS (+FAB, MeOH/NBA): m/e (rel. intensity) 817 (16), 816 (32), 815 (30), 814 (71), 813 (43), 812(100), 811 (67), 810 (27), 809 (2), 808 (3) [the peaks m/e=816, 814, 812, 811, 810, 808 correspond to the cation C$_{46}$H$_{40}$F$_2$NP$_2$Pd of the salt with the palladium isotopes (frequency of natural occurrence) $^{110}$Pd (43.2), $^{108}$Pd (97.7), $^{106}$Pd (100), $^{105}$Pd (81.3), $^{104}$Pd (40.1) or $^{102}$Pd (3.5)]; IR (KBr): 3060 (w), 1450, 1442, 1418, 841, 746, 697, 556, 502 cm$^{-1}$.

Crystals: 0.3×0.2×0.15 mm$^3$ cell dimensions: a=12.091 (1), b=18.612(4), c=18.958 (2) Å, P2$_1$2$_1$2$_1$, Z=4, D$_x$=1.391 mg/m$^3$; λ(mo K$_{60}$)=0.7107 Å, θ$_{max}$=25.0°, 8124 individual reflections, 4722 with (Fo)>4σ; 533 parameters, wR2=0.076 (all reflection), R1 =0.047 (4722 reflections), S=0.83, maximum and minimum in the differential Fourier synthesis: 0.88, –0.61 e/Å$^3$.

{(S)-2)[1-(Dimethylamino)ethyl]-phenyl-C,N} [(R)-6,6'-di-fluorobiphenyl-2,2'-diyl) bis(diphenylphosphine)]palladium(II) chloride (S,R)-(+)-10

The original filtrate from the preparation of (S,S)-(–)-10 (see above) was evaporated under vacuum to give a pale yellow solid (3.25 g, 3.83 mmol, yield 104% of the theoretical value); m.p. 162°–165° C. (decomposition); $[\alpha]^{25}_D$ +184.3 (c=1.02, methanol). $^1$H-NMR signals of its diastereomer (S,S)-10 were not detected, and no traces were detected with TLC (diastereoselectivity >>99:1). The crude complex was dissolved in deoxygenated methanol (40 ml) and the solution was boiled under reflux for 2 min. Deoxygenated water (150 ml) was added, and the mixture was left to stand in the sealed flask for 8 h. The precipitate was collected by filtration, washed with deoxygenated methanol/water (1:8, 15 ml) and water (30 ml) and dried under vacuum: pale yellow crystals (3.00 g, 3.54 mmol, 96% yield), m.p. 164°–166° C. (decomposition), $[\alpha]^{25}_D$ +208.0 (c=1.01, methanol; $^1$H-NMR (200 MHz, CD$_3$OK); δ2.05 (d, J=1.9 Hz, 3H, NCH$_3$), 2.17 (m, ca. t, J≈3.3 Hz, 3H, NCH$_3$), 2.27 (d, J=6.3 Hz, 3H, NCHCH$_3$), 3.58 (qui. J=6.3 Hz, 1H, NCHCH$_3$), 6.26 (tdt, J=7.5, 2.5 and 1.3 Hz, 1H), 6.44 (qua d, J=7.5 and 0.8 Hz), 6.66–6.85 (m, 4H), 6.96–7.76 (m, 24H); $^{31}$P{$^1$H}-NMR (145.79 MHz, CD$_3$OD) δ+10.72 (dd, $^2$J$_{P,P}$=44 Hz, $^4$J$_{P,F}$=7.6 Hz), 33.21 (dd, $^2$J$_{P,P}$=44 Hz, $^4$J$_{P,F}$=7.5 Hz); $^{19}$F{$^1$H}-NMR (376.50 MHz, CD$_3$OD): δ–103.37 (qua. $^4$J$_{F,P}$=$^4$J$_{F,F}$=6.8 Hz), –104.46 (≈qua d, $^4$J$_{F,P}$=$^5$J$_{F,F}$=6.8 Hz, $^5$J$_{F,P}$=2 Hz); MS (+FAB, MeOH/NBA): identical with MS of (S,S)-10.

[(S)-(6,6'-Difluorobiphenyl-2,2'-diyl)bis(diphenylphosphine)]palladium(II) dichloride (S)-(–)-11

Deoxygenated 10 N hydrochloric acid (12 ml) was added to a solution, boiling under reflux, of (S,S)-(–)-10 (1.12 g, 1.17 mmol) in deoxygenated acetone (20 ml). After a few minutes, a yellow precipitate formed. The mixture was boiled under reflux for 2 h and then concentrated under vacuum to 10 ml. Deoxygenated water (100 ml) was added, and nitrogen was bubbled through the suspension (25° C., 10 min). The solid was collected by filtration and stirred with isopropanol/water (1:1, 20 ml) for 5 min. The solid was filtered, washed with isopropanol/water (1:1, 5 ml), and dried under vacuum to give bright yellow crystals (846 mg, 1.15 mmol, yield 98%), m.p. 310°–312° C. (decomposition), $[\alpha]^{25}_D$ –311.9 (c=0.495, dichloromethane); the specific rotation was unchanged after the solution had been allowed to stand at ambient temperature for 8 days; $^1$H-NMR (200 MHz, CDCl$_3$): δ6.66–6.86 (m, 4H), 6.90–7.08 (m, 2H), 7.27–7.56 (m, 12H), 7.70 (ddd, J=12.5, 8.0, 2.0 Hz, 4H), 7.94 (dd, J=12.5 and 8.0 Hz); $^{31}$P{$^1$H}-NMR (145.79 MHz, CDCl$_3$): δ26.72 (br d, $^4$J$_{P,F}$=6.0 Hz); $^{19}$F-NMR (188.14 MHz, CDCl$_3$): δ–108.5 (m); MS (+FAB, MeOH/NBA): m/e (rel. intensity) [705 (14), 704 (20), 703 (53), 702 (37), 701 (93), 700 (49), 699 (100), 698 (60), 697 (30) M-Cl for various isotopes of Pd and Cl], [668 (7), 667 (11), 666 (14), 665 (10), 664 (23), 663 (16), 662 (10) M-2Cl for various isotopes of Pd]; IR (KBr): 3060 (w), 1450, 1437, 1420, 747, 696, 507, 499, 487 cm$^{-1}$, elemental analysis (found/calculated for C$_{36}$H$_{26}$Cl$_2$F$_2$P$_2$Pd): C 58.9/58.76, H 3.8/3.56, Cl 9.6/9.64, F 4.7/5.16.

[(R)-(6,6'-Difluorobiphenyl-2,2'-diyl)bis(diphenylphosphine)]palladium(II) dichloride(R)-(+)-11

Deoxygenated 10 N hydrochloric acid (22 ml) was added to the solution, boiling under reflux, of (S,R)-(+)-10 (408 mg, 0.48 mmol) in deoxygenated acetone (20 ml). After a few minutes a yellow precipitate formed. The mixture was boiled under reflux for 2 h. Treatment as described for (S)-11 gave bright yellow crystals (346 mg, 0.47 mmol, 98% yield), m.p. 310°–311° C. (decomposition), $[\alpha]^{25}_D$ +311.5 (c=0.495,dichloromethane); the spectra were identical to those of (S)-11.

(S)-(6,6'-Difluorobiphenyl-2,2'-diyl)bis(diphenylphosphine) (S)-(+)-5

1,2-bis(Diphenylphosphino)ethane (ddpe) (508 mg, 127 mmol, 0.8 equivalent) was added to a solution of (S,S)-10 (1.53 g, 1.59 mmol) in deoxygenated dichloromethane (20 ml). The resulting clear solution was stirred at 20°–25° C. for 16 h. The course of the reaction was monitored by TLC

[100% toluene, $R_f$: (S,S)-10 (0.00), dppe (0.61), 5 (0.80)], indicating a quantitative reaction of ddpe, the presence of 5 and a base line spot (palladium complexes). Deoxygenated cyclohexane (20 ml) was added, and the mixture was filtered over a frit containing a bed of silica gel (35–70 μm, 13.5 g). The silica bed was washed with deoxygenated dichloromethane/cyclohexane (1:1, 4×20 ml). The filtrates were combined and concentrated by evaporation under vacuum. Methanol (3 ml) was added to the residue, and the solvent was concentrated by evaporation under vacuum to give a colorless solid (657 mg, 1.18 mmol, yield 93%), m.p. 161°–163° C. An analytical sample was prepared by recrystallization (0° C., 12 h) from boiling toluene/ethanol (4:5), m.p. 164°–165° C., $[\alpha]^{25}_D$ +114.9 (c=0.99, toluene), cf. Table 1. The NMR spectra were identical with those of (R/S)-5. TLC and HPLC [cf. (R/S)-5] indicated 100% chemical purity. Oxidation to give the bisphosphine oxide) (S)-4 with subsequent HPLC analysis of the chiral phase indicated 100% ee (see below). When (S,S)-10 was reacted under the same conditions as 1.0 equivalent of dppe, considerable quantities of dppe were untreated (TLC) and it was difficult to remove them from the reaction product.

Configurational stability of (S)-5 on heating in solution

A solution of optically pure (S)-5 (44.2 mg) in tetralin (10 ml, boiling point 207° C.) was boiled under reflux for 2.5 hours in an argon atmosphere. The specific rotation of the solution remained constant, and a sample withdrawn following the oxidation to bis(phosphine oxide) (S)-4 indicated 100% as in accordance with HPLC analysis of the chiral phase.

The configurational stability was likewise observed when a solution of (S)-5 in toluene was left to stand under argon for 12 days, and this solution was then heated at 100° C. for 8 h, and when a solution of (S)-5 was boiled under reflux in mesitylene (boiling point 164° C.) for 3 h.

Experiment on the preparation of (S)-5 by reaction of palladium dichloride complex (S)-11 with potassium cyanide Potassium cyanide (30 mg, 0.46 mmol), water (5 ml) and methanol (10 ml) were added to a solution of (S)-11 (87 mg, 0.12 mmol) in dichloromethane (10 ml) (all solvents deoxygenated). The clear solution was stirred for 2 h. TLC indicated no formation of 5. Potassium cyanide (250 mg) was added and the solution was stirred for 16 h: no reaction.

(R)-(6,6'-Difluorobiphenyl-2,2'-diyl)bis(diphenylphosphine) (R)-(–)-5

In a process analogous to that described for (S)-(+)-5, the reaction of the chloride (S,R)-10 (748 mg, 0.88 mmol) with dppe (282 mg, 0.71 mmol, 0.8 equivalent) in dichloromethane (20 ml) gave the title compound (390 mg, 0.07 mmol, yield 99%), m.p. 164°–165° C., $[\alpha]^{25}_D$ –114.8 (c=1.03, toluene), NMR spectra identical with those of (R/S)-5 and (S)-5. TLC and HPLC indicated a 100% chemical purity. The oxidation to give the bis(phosphine oxide) (R)-4 with subsequent HPLC analysis of the chiral phase indicated 100% ee (see below).

(S)-6,6'-Difluorobiphenyl-2,2'-diyl)bis(diphenylphosphine oxide) (S)-(–)-4

Methanol (5 ml) and then 35% strength hydrogen peroxide solution (1 ml, 11.6 mmol) were added to a solution of (S)-5 (101 mg, 0.18 mmol) in toluene (2 ml). The mixture was stirred for 4 h. TLC [cf. (R/S)-5] indicated the title compound and, in traces, residues of 5 and monooxide. Hydrogen peroxide (1 ml) was added, and stirring was continued for 1 h. TLC then indicated quantitative oxidation. The solution was washed with saturated aqueous sodium sulfite solution (3×3 ml) and 1 N hydrochloric acid (2×2 ml). The solvent was evaporated under vacuum. The residue was extracted with chloroform (3×15 ml). The extracts were combined, washed with saturated aqueous sodium bicarbonate solution (2×10 ml) and with water (2×10 ml) and dried over magnesium sulfate. The solvent was evaporated under vacuum to give a colorless solid (100 mg, 0.17 mmol, yield 94%), m.p. 275°–277° C., $[\alpha]^{20}_D$ –11.8° (c=0.92, chloroform). $^1$H-NMR (Table 2); $^{13}$C-NMR (Table 3); $^{19}$F{$^1$H}-NMR (470.59 MHz, CDCl$_3$): δ–110.21 ($J_{F,P}$=6.6 Hz); $^{31}$P{$^1$H}-NMR (202.46 MHz, CDCl$_3$): δ28.89 ($J_{F,P}$=6.6 Hz).

TABLE 2

| Signal | Intensity δ (ppm) | (n)$J_{H,H}$ (Hz) coupling partner | (n)$J_{H,F}$ | (n)$J_{H,P}$ | $^1J_{C,H}$ |
|---|---|---|---|---|---|

$^1$H-NMR [500 MHz, 10 mg of (S)-(–)-4/ml of CDCl$_3$]

TABLE 3

| Signal | Intensity δ (ppm) | m $^1$H | m $^{19}$F | m $^{31}$P |
|---|---|---|---|---|

$^{13}$C{$^1$H}-NMR [125.76 MHz, 50 mg (S)-(–)-4/ml of CDCl$_3$]

HPLC of the chiral phase (250×4.6 mm DNBPG-Bakerbond, 1.0 ml/min n-hexane+ethanol (20+1), detection at 254 nm) in comparison with the racemic reference sample (R/S)-4 indicated 100% of (S)-4 ($t_{ret}$ 25.50 min) and 0% of (R)-4 ($t_{ret}$ 23.63 min). An analytical sample was obtained by recrystallization (0° C., 12 h) from boiling dichloromethane/ethyl acetate (3:1), m.p. 282°–283° C., $[\alpha]^{20}_D$ –11.3 (C=0.96, chloroform); $[\alpha]^{20}_{365}$ +57.0 (c=0.59, methanol).

(R)-6,6'-Difluorobiphenyl-2,2'-diyl)bis(diphenylphosphine oxide) (R)-(+)-4

Analogously, the oxidation of (R)-5 gave a colorless solid, m.p. 282°–283° C., $[\alpha]^{20}_D$ +11.3 (c=0.83, chloroform); $[\alpha]^{20}_{365}$ –56.5 (c=0.57, methanol). The $^1$H—, $^{13}$C{$^1$H}—, $^{19}$F{$^1$H}— and $^{31}$P{$^1$H}-NMR spectra in CDCl$_3$ were identical with those of (S)-4 and (R/S)-4. HPLC of the chiral phase indicated 100% of (R)-4.

Rhodium(I)-(R)-(–)-5-catalyzed asymmetric hydroboration/oxidation of p-methoxystyrene A solution of p-methoxystyrene (12) (671 mg, 5.0 mmol), (1,5-cyclooctadiene) (2,4-pentanedionato)rhodium(I) (31.0 mg, 0.10 mmol) and (R)-(–)-5 (61.4 mg, 0.11 mmol) in deoxygenated dry THF (6 ml) is boiled under reflux for 90 min in argon. The solution is then cooled, and a 1 N solution of catecholborane in THF (10.0 ml, 10.0 mmol) flushed beforehand with argon (10 min) is added dropwise at 0° C. over the course of 5 min. The mixture is stirred under argon at 0° C. for 90 min. TLC (cyclohexane/ethyl acetate 1:1; $R_f$12: 0.66, 13: 0.41, 14:0.30) indicates the quantitative reaction of 12. The solution is cooled to –20° C., and ethanol (10 ml), 4 N aqueous sodium hydroxide solution (5 ml) and 36% strength aqueous hydrogen peroxide solution (10 ml)

are added in succession at ≦5° C. The mixture is stirred overnight at ambient temperature and is then subjected to extraction with diethyl ether (3×50 ml). The extracts are combined and washed with 1 N sodium hydroxide (4×25 ml), with water (20 ml) and with brine (20 ml) and dried over sodium sulfate, and the solvent is evaporated. The residue (780 mg of pale brown oil) is subjected to molecular distillation (bar 60°–80° C./≈10$^{-3}$ torr) to give a colorless oil (682 mg, 4.48 mmol, yield 90%) and a brown residue which crystallizes (98 mg). TLC and $^1$H-NMR indicate that the distillate consists of 13 and 14 (ratio 78:22), $[\alpha]^{20}_D$ +27.7° (c=1.17, chloroform). Correction for 22% achiral 14 gives $[\alpha]^{20}_D$ (corrected) ±35.5° (c=0.91, chloroform). Comparison with the literature [30] indicates that 13 has ≈67% ee of the (R)-configuration. HPLC analysis of the chiral phase (250 mm length, 4.6 mm internal diameter, Chiralcel OD column, 10 μm (Daicel); 0.5 ml/min, n-hexane/ethanol (100+0.8), 40° C., detection at 254 nm] gives 68.3% (R)-(+)-13 ($t_{ret}$ 62.80 min), 8.5% (S)-(–)-13 (79.40 min) and 23.2% of 14 (66.14 min). This corresponds to 77.8% ee of the (R)-(+)-isomer of 13.

Hydrogenation of 2-benzylidenesuccinic acid 4-[(4-BOC-amino)-1-piperidide, catalyzed by the neutral rhodium(I)-(R)-(–)-5 complex (R)-(–)-5 (30.1 mg, 0.054 mmol) is added to the suspension of di-μchlorobis[(cycloocta-1c,5c-diene) rhodium(I)] (12.3 mg, 0.025 mmol) in deoxygenated methanol/benzene (3:1) (20 ml) and is stirred under argon so as to produce a clear solution within 15 min. In a hydrogenation flask, 2-benzylidenesuccinic acid 4-[(4-BOC-amino)-1-piperidide][53] (1.94 g, 5.0 mmol) is dissolved in deoxygenated methanol/benzene (3:1) (20 ml). The clear catalyst solution is added under argon and the reaction mixture is agitated under 1 bar of hydrogen from a hydrostatic hydrogenation apparatus[53]: over the course of 6 h no hydrogen is taken up. The hydrogenation flask is placed under argon in an autoclave incorporated agitation[53] and subjected for 2 days to 150 bar of hydrogen. The solvent is evaporated under vacuum and the solid residue is dissolved in tert-butyl methyl ether (40 ml). The cold (0° C.) solution is washed with 0.5 N hydrochloric acid (10 ml) and with water (10 ml) and dried (MgSO$_4$).

The solvent is evaporated, and a solid (1.80 g, 4.16 mmol, 92% crude yield) is obtained. HPLC[53] indicates quantitative hydrogenation. HPLC of the chiral phase[53] indicates 22% ee of the (R)-(+)-configuration.

I claim:

1. A compound of the formula I

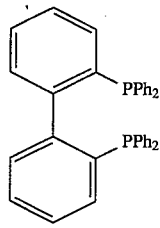

I in which the phenyl rings of the biphenyl molecule are substituted with from 1 to 8 atoms selected from the group consisting of fluorine, chlorine, and a mixture thereof, at least two of said atoms being fluorine.

2. A compound of the formula II

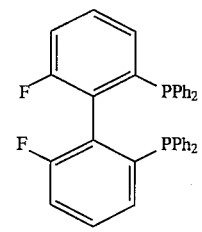

II

3. A process for the preparation of a compound of the formula I as claimed in claim 1 which comprises reacting a compound of the formula 4

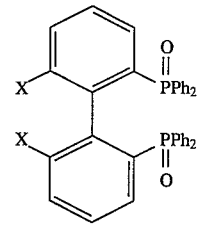

4 in which X is F or Cl, with Cl$_2$Si and NBu$_3$, in an organic solvent under an inert gas or alternatively boiling the compound of the formula 4 under reflux with HSiCl$_3$ and NBu$_3$ in an organic solvent to give the compound of the formula I, where the phenyl rings of the biphenyl molecule are unsubstituted or substituted with up to 6 additional atoms selected from the group consisting of fluorine, chlorine, and a mixture thereof.

4. A process for the preparation of a compound of the formula 4 as claimed in claim 3, which comprises heating a compound of the formula 3

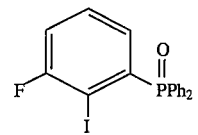

3 in an inert solvent with the addition of a transition metal, where the compound of the formula 3 ie unsubstituted or substituted 1, 2, or 3 times with atoms selected from the group consisting of fluorine, chlorine, and a mixture thereof.

5. A process for the preparation of a compound of the formula 3 as claimed in claim 4, which comprises reacting a compound of the formula 2

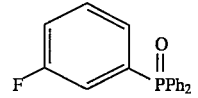

2 with lithium diisopropylamide in an inert solvent, and then with iodine, where the compounds of the formulae 2 or 3 are unsubstituted or substituted 1, 2, or 3 times with atoms selected from the group consisting of fluorine, chlorine, and a mixture thereof.

6. A process for the preparation of a compound of the formula 2 as claimed in claim 5, which comprises reacting a compound of the formula 1

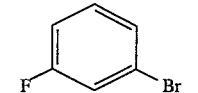

1 with n-butyllithium in an organic solvent, then with Ph$_2$PCl and subsequently with H$_2$O$_2$ in an alcohol, where the compounds of the formulae 1 and 2 are unsubstituted or substituted 1, 2, or 3 times with atoms selected from the group consisting of fluorine, chlorine, and a mixture thereof.

7. A compound of the formula 4

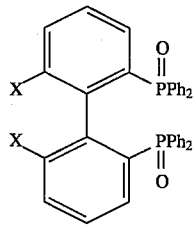

in which X is F or Cl and in which the phenyl rings of the biphenyl molecule are unsubstituted or substituted with up to 6 additional atoms selected from the group consisting of fluorine, chlorine, and a mixture thereof.

8. A compound of the formula 4 as claimed in claim 7 wherein X is F.

9. A process as claimed in claim 3 wherein X in the compound of formula 4 is F.

10. A compound of the formula II as claimed in claim 2 wherein the phenyl rings of the biphenyl molecule are substituted with up to 6 atoms selected from the group consisting of fluorine, chlorine, and a mixture thereof.

11. A complex of rhodium(I), ruthenium(II), palladium(II) or palladium(0) with a compound of the formula II

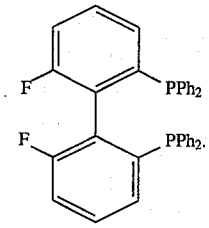

12. A process for the preparation of a complex as claimed in claim 11, which comprises reacting a compound of the II with a complex having a readily displaceable ligand, or comprises obtaining the complex of claim 11 from a corresponding palladium complex having an N,N-dimethyl-α-phenylethylamine ligand by HCl-induced elimination of the N,N-dimethyl-α-phenylethylamine ligand.

13. A catalyst comprising a complex as claimed in claim 11.

14. A catalyst for symmetrical addition, asymmetrical addition, substitution, rearrangement, or coupling reactions comprising a complex as claimed in claim 11.

* * * * *